United States Patent [19]

Hein et al.

[11] Patent Number: 5,423,761
[45] Date of Patent: Jun. 13, 1995

[54] CLOSING SYSTEM FOR A PASSAGE FOR INSTRUMENTS

[76] Inventors: Peter Hein, Stedinger Str. 4, DE-0-1615 Zeuthen; Helmut Laser, Rykestr. 17, DE-0-1055 Berlin, both of Germany

[21] Appl. No.: 78,264
[22] PCT Filed: Oct. 24, 1992
[86] PCT No.: PCT/EP92/02439
§ 371 Date: Jun. 28, 1993
§ 102(e) Date: Jun. 28, 1993
[87] PCT Pub. No.: WO93/08728
PCT Pub. Date: May 13, 1993

[30] Foreign Application Priority Data

Oct. 31, 1991 [DE] Germany .................. 41 35 983.6

[51] Int. Cl.$^6$ ............... A61B 1/00; A61M 39/00
[52] U.S. Cl. .................. 604/167; 604/169; 604/247; 251/65; 251/149.2
[58] Field of Search .......... 606/167, 185; 604/167, 604/169, 247, 256; 137/527.6; 251/65, 149, 149.1, 149.2

[56] References Cited

U.S. PATENT DOCUMENTS

| | | | |
|---|---|---|---|
| 2,949,931 | 8/1960 | Ruppright | 251/65 |
| 3,265,062 | 8/1966 | Hesse | 251/65 |
| 3,370,305 | 2/1968 | Goott et al. | 251/65 |
| 3,891,000 | 6/1975 | Melnick | 251/65 |
| 4,535,773 | 8/1985 | Yoon | 604/169 |
| 5,104,383 | 4/1992 | Shichman | 604/167 |

FOREIGN PATENT DOCUMENTS

| | | |
|---|---|---|
| 0198407 | 10/1986 | European Pat. Off. . |
| 0515220A1 | 11/1992 | European Pat. Off. . |
| 7430345 | 12/1974 | Germany . |
| 2800607 | 10/1978 | Germany . |
| 3242870 | 6/1983 | Germany . |
| 1482857 | 8/1977 | United Kingdom ........... 604/167 |

Primary Examiner—Ralph A. Lewis
Attorney, Agent, or Firm—Jordan and Hamburg

[57] ABSTRACT

A closing system for an instrument passage, particularly for use in laparoscopic puncture devices. The object of the invention is to provide a closing system of safe operation which permits a non-complicated cleaning and has a simple and comparatively small construction. The object is realized according to the invention in that a closing member is a floatingly seated disc which centrally fits into a conical seat and which is held in any position only by a non-symmetrically acting magnetic force of at least one magnet, preferably a permanent magnet.

11 Claims, 2 Drawing Sheets

CLOSING SYSTEM FOR A PASSAGE FOR INSTRUMENTS

BACKGROUND OF THE INVENTION

The invention relates to a closing system for an instrument passage particularly for use in laparoscopic incision devices and for a closing instrument and cleansing ducts. Various closing systems for instrument passages are known and operating on different principles. Said known closing systems exhibit the following disadvantages:

The closing system known as a "trumpet valve" has to be operated manually when an instrument is inserted and has to be disassembled for cleaning. The manufacture of the "trumpet valve" is expensive and its components require high precision in manufacture. The closing system known as an automatic flap valve includes a flap mounted on a thin axle, said flap is set into the closing position by means of a spring. It is complicated to clean the flap mounted as described hereinbefore. A damaging of the front lens of an endoscope cannot be excluded when the latter is rapidly passed through.

The utility model DE-GM 74 30 345 discloses a closing system in which a flap is pivotally seated, which flap is set into the closing position by a permanent magnetic means. Cleaning is as difficult as in the foregoing devices.

The German patent specification DE 32 42 870 A1 discloses a closing system, one embodiment of which provides a laterally and pivotally seated flap which includes an annular magnet which cooperates with an annular magnet to a flap mount. In order to protect instruments against damage, when passed through, the flap is coated with plastics. This solution has the disadvantage, as concerns the non-pivotally seated flap embodiments, if ferro-magnetic instruments are passed it might occur that the latter takes the flap along. This is on the one hand an obstacle to the operator and, on the other hand, does not ensure a safe closing of the flap after the retraction of the instrument. Furthermore in the Patent specification DE 28 00 607 A1 an operation laparoscope is described in which the closing is effected by means of a ferro-magnetic sphere which is attracted by an annular magnet in the valve-seating so that the ferro-magnetic sphere if funneled into a cone-shaped valve seat. When, in this solution, instruments having a plane front face are passed, an entire disarrangement of the sphere may very easily occur so that a safe closing is not ensured after the retraction of the instrument. In order to prevent such a disarrangement, the aforementioned specification requires the use of instruments being provided with specially shaped front faces which laterally displace the sphere in the cone-shaped seat and which require protection means for the optical systems of, for example, an endoscope. Such measures involve considerable technical expenditures. However, optical systems of conventional endoscopes can be damaged by the aforesaid solution just as with conventional sphere valves. A closing system as shown in DE 28 00 607 A1 can be easily cleaned, out is bulky. The entire system is heavy due to the large mass of the sphere which, in turn, requires a high magnetic force.

SUMMARY OF THE INVENTION

It is an object of the present invention to provide a closing system for an instrument passage in the field of art which ensures apart from a high locking reliability a simple cleaning and a simple and safe assembly of the components. It is a further object of the present invention to embody the closing system in a manner which eliminates any kind of damage otherwise possible to occur to the head lenses of an endoscope when passing the locking system, and this being achieved without any additional protective means on the instruments.

According to the invention these objects are realized by the features of the claims disclosed hereinafter.

The closing system of the present invention comprises a magnet, preferably a permanent magnet, a member for directing the magnetic flux and a closing member, hereinafter referred to as a flap. Said permanent magnet and said member for directing the magnetic flux constitute the two magnetic poles, said displaceably and floatingly seated flap closes the magnetic circuit.

Advantageously, the permanent magnet has the shape of an annular sector enclosing the instrument passage and is connected to the circular magnetic flux director which constitutes via an axial annular segment portion the other magnetic pole. When a force acts upon the flap in an opening direction said flap pivots about an axis which is adjacent the stronger magnetic pole constituted by the permanent magnet. Alternatively, the non-symmetrical magnetic force acting upon the flap is achieved by a plurality of permanent magnets being circumferentially arranged in a manner to effect a strong non-symmetrical magnetic field. Thus, it is ensured that the ferromagnetic flap is pivoted about an axis adjacent the permanent magnet when instruments are passed through or retracted. Due to the fact that the flap does not contain a magnet it is eliminated that the flap is taken along when ferromagnetic instruments are passed through. Furthermore, due to the non-symmetrical distribution of the magnetic field, it is eliminated that the flap is entirely removed from the seating when instruments are passed which have a plane head face. Advantageously, the radius of the flap is not essentially larger than the distance of the permanent magnet from the axis of the instrument passage thus a safe pivoting from the open position into the closing position is achieved.

The axial symmetry of the closing system chamber, the easy removal of the flap therefrom against the magnetic force, and the absence of any pivots or springs permit a simple and non-complicated cleaning of the puncture device and the components of the closing system.

The subject of the invention is not restricted to the circular shape of the flap. It is feasible, for example, to embody the flap as a chamfered circular disc or even to embody it in a rectangular or square shape. When embodied in this manner it has to be ensured that one of the straight edges is adjacent to the permanent magnet.

In order that the invention may be more readily understood reference is made to the accompanying drawings which illustrate diagrammatically and by way of example the inventive solution.

DETAILED DESCRIPTION OF THE INVENTION

Figure 2:
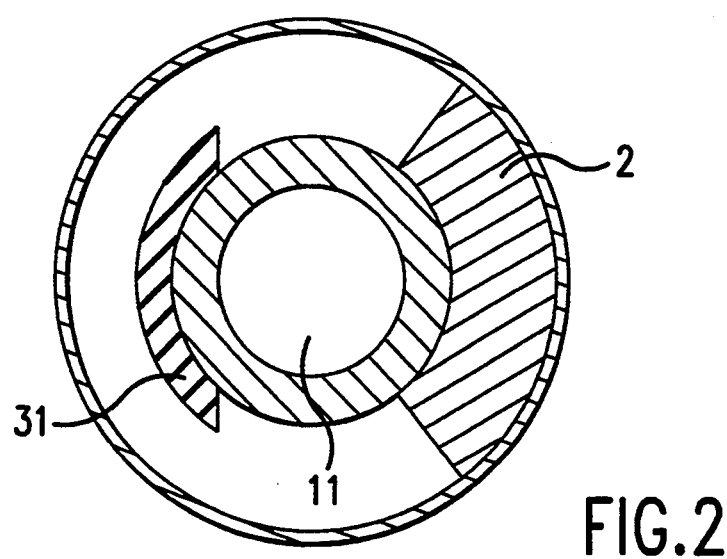

According to FIG. 2, permanent magnet 2 of annular segment shape contacts an instrument passage 11. The permanent magnet 2 is connected to a flux director 3, an annular segment portion 31 of which is in diametral opposition to the permanent magnet 2. The permanent magnet 2 and the portion 31 constitute the two magnetic poles of a magnetic circuit, closed by flap 4.

The particular arrangement of the permanent magnet 2 and of the flux director 3 ensures that a non-symmetrical magnetic field acts upon the flap 4. The pivot axis of the flap 4 is defined adjacent to and within the range of the permanent magnet 2, due to the stronger magnetic field intensity of the latter, whereas the flap is lifted on the opposite side when an instrument is passed. Moreover, the particular arrangement of the magnetic system ensures that the flap 4 safely returns into a conical valve seat 12 which via its circumferential portion encloses the flap 4. Due to the fact that the magnetic feedback is established via the rim portions of the flap 4, that is, when, for example, a round-shaped flap is used the diameter is not considerably larger than the diameter of the instrument passage, it is ensured that the flap 4 is not permitted to take any other stable position than that of the closing position.

The indentations 41 and 42 provided on respective faces of the flap 4 ensure that the head lenses of an endoscope objective are not damaged when the flap 4 is pushed open. Advantageously, the indentations 41 and 42 are provided on both faces of the flap 4 to enable an installation thereof independent of the position.

Figure 1:
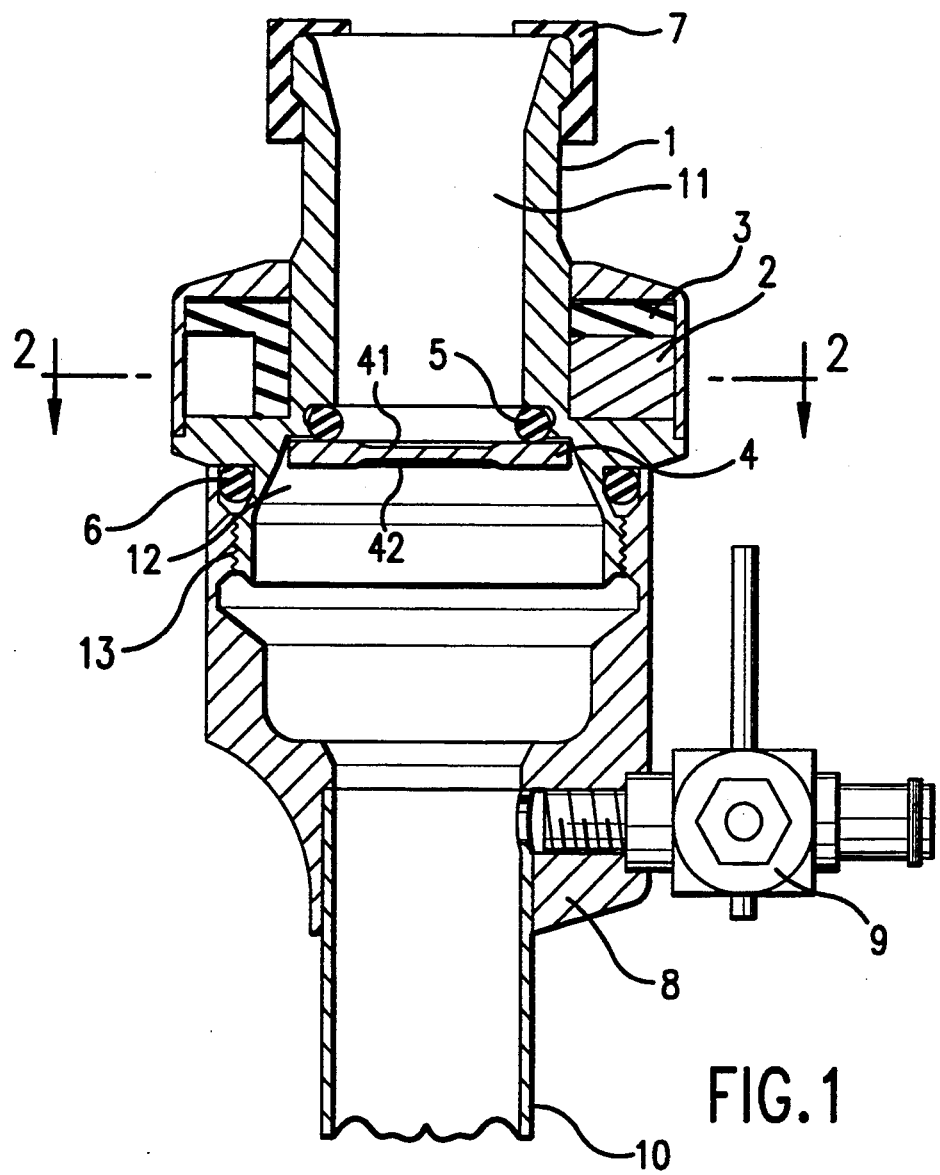
FIG. 1 shows a laparoscopical punture device including the inventive closing system, FIG. 2 a sectional view of the device of FIG. 1 along the line A—A, and FIG. 3 two puncture devices of different diameter one inserted into the other for reducing the instrument passage.

A laparoscopic puncture device according to FIG. 1 comprises a valve housing 1, the flap 4 and a chamber housing 8 with a cock 9. The chamber housing 8 is connected to a tube 10. The chamber housing 8 and the valve housing 1 are connected airtight via a thread 13 and a sealing ring 6. The valve housing 1 is provided with an elastic sleeve 7 at the entrance of the instrument passage 11. In the interior of the valve housing 1, a magnet system is arranged being constituted of the permanent magnet 2 and the flux director 3 to which an annular segment portion 31 is attached. At the outlet of the instrument passage 11 the valve housing 1 has a cone-shaped valve seat 12 which is provided with a sealing ring 5. The flap 4 is attracted towards the sealing ring 5 by the magnetic force and thus seals a human body interior against ambience. The cone-shape of the valve seat 12 defines the position of the flap 4. The valve seat 12 is adapted to the external geometry of the flap 4. In order to clean and disinfect the puncture device, the valve housing 1 and the chamber housing 8 are detached from one another by unscrewing and the flap 4, which is moveable at will, is taken off against the magnetic force.

Figure 3:
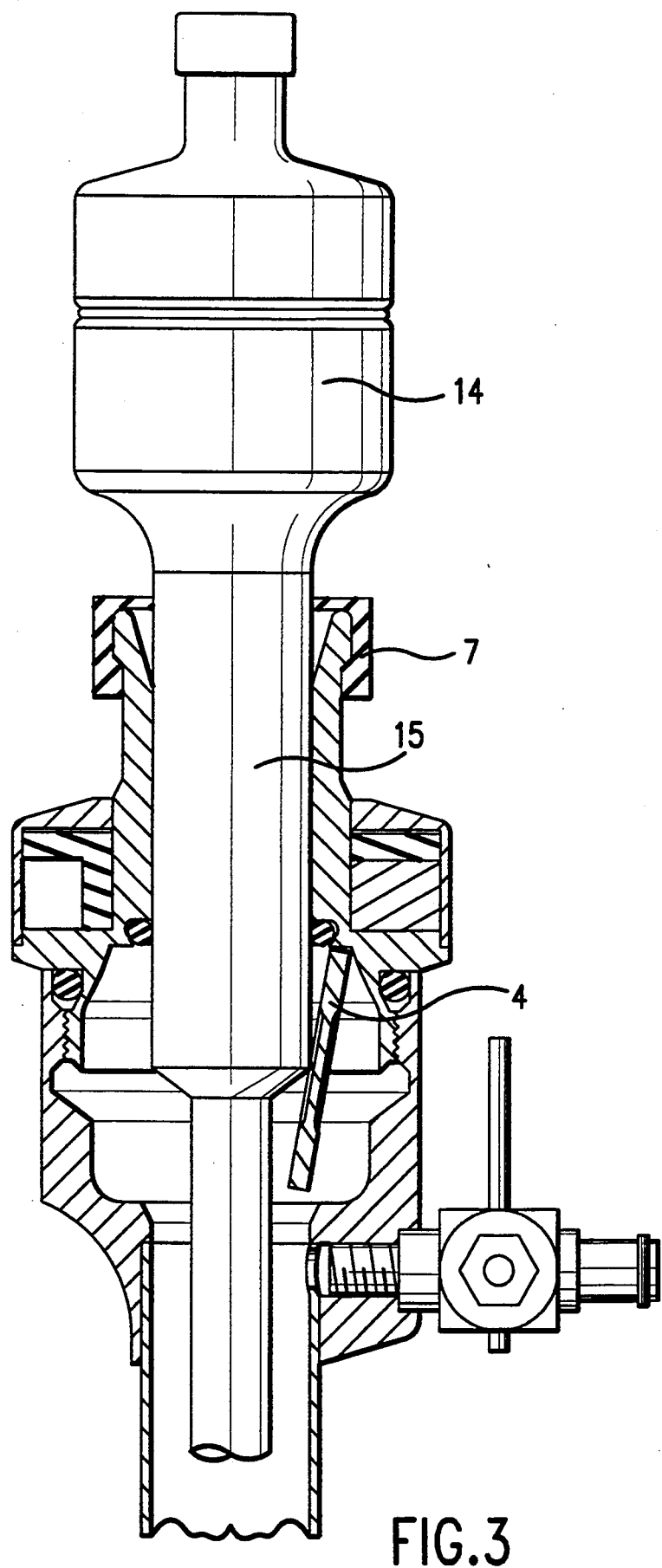

Very often in the course of an operation it is necessary to reduce the diameter of the puncture device for introducing instruments of lower diameter. The conventionally employed reducer sleeves in most cases open the valve of the puncture device so that considerable gas losses occur when the instruments are exchanged. According to an advantageous solution, as shown in FIG. 3, a puncture device for thinner instruments is embodied in a manner that an additional cylindrical shaft 15 is provided which fits into the instrument passage of the larger puncture device. A washer 7 seals the instrument passage of the larger puncture device against the cylindrical shaft 15. Since the puncture device 14 also includes a valve as described hereinbefore the exchange of instruments can be carried out without a relevant loss of gas. Due to the fact that the puncture device 14 can be employed as a complete device, apart from being used as a reduction means, the number of devices required for an operation can be substituted for more universally applicable instruments.

We claim:

1. A closing system for an instrument passage comprising a conical seat at one end of the passage; a ferromagnetic closing member being fitted into the conical seat, the closing member being floatingly seated in the conical seat, the closing member having a circumferential portion; a magnet being arranged so that an area of strongest magnetic force of the magnet is directed at a section of the circumferential portion of the closing member for providing an asymmetric magnetic force, whereby the section of the circumferential portion of the closing member at which the magnet is directed remains seated in the conical seat when the closing member is moved for opening the passage; and a ferromagnetic flux directing member being arranged adjacent the magnet, the flux directing member having an annular segment portion arranged in diametral opposition to the area of strongest magnetic force of the magnet, thereby forming a magnetic circuit having the magnet as one pole and the annular segment portion of the flux directing member as another pole, the closing member operating to close the magnetic circuit, the flux directing member operating to provide for magnetic feedback in the circumferential portion of the closing member so that the closing member is most stable when in a closed position.

2. A closing system as claimed in claim 1, wherein the permanent magnet has an annular segment base face, concentrically attached to said instrument passage.

3. A closing system as claimed in claim 1, wherein the ferromagnetic flux directing member is annular and is concentrically attached to the instrument passage.

4. A closing system as claimed in claim 1, wherein the closing member has an indentation in at least one of its surfaces coincident with a central axis of the instrument passage.

5. A closing system as claimed in claim 1, wherein the closing member is a circular disc.

6. A closing system as claimed in claim 5, wherein a diameter of the closing member is not considerably larger than a diameter of the instrument passage for making a most stable position of the closing member a closed position.

7. A laparoscopic puncture device having an instrument passage, the instrument passage having the closing system of claim 1.

8. A laparoscopic puncture device as claimed in claim 7, further comprising a shaft in the instrument passage.

9. A laparoscopic puncture device as claimed in claim 8, wherein the shaft is cylindrically shaped.

10. A closing system as claimed in claim 1, wherein a radius of the closing member is not essentially larger than a distance between the magnet and a central axis of the instrument passage for pivoting the closing member between an open and a closed position.

11. A closing system as claimed in claim 1, wherein the magnet is a permanent magnet.

* * * * *